(12) United States Patent
Na et al.

(10) Patent No.: US 6,221,358 B1
(45) Date of Patent: Apr. 24, 2001

(54) METHOD FOR LOWERING BLOOD ALCOHOL CONCENTRATION BY ADMINISTERING AN EXTRACT OF *RHUS VERNICIFLUA*

(75) Inventors: Chun-Soo Na; Nam-Chul Jung, both of Suwon (KR)

(73) Assignee: Forestry Research Institute, Seoul (KR)

( * ) Notice: Subject to any disclaimer, the term of this patent is extended or adjusted under 35 U.S.C. 154(b) by 0 days.

(21) Appl. No.: 09/497,047

(22) Filed: Feb. 2, 2000

Related U.S. Application Data (63) Continuation-in-part of application No. 09/063,853, filed on Apr. 21, 1998, now Pat. No. 6,099,845.

(30) Foreign Application Priority Data

Aug. 1, 1997 (KR) .................................. 97-36844

(51) Int. Cl.$^7$ ............................ A01N 65/00; A61K 35/78
(52) U.S. Cl. ........................................ 424/195.1; 514/783
(58) Field of Search .......................... 424/195.1; 514/783

(56) References Cited

U.S. PATENT DOCUMENTS 5,624,910 * 4/1997 Vallee et al. ........................ 514/27

* cited by examiner

*Primary Examiner*—Herbert J. Lilling
(74) *Attorney, Agent, or Firm*—Rosenman & Colin, LLP (57) ABSTRACT

A method for lowering blood alcohol concentration by administering an extract of *Rhus verniciflua* to human, thereby preventing or treating a disease state caused by intake of an alcohol.

3 Claims, 6 Drawing Sheets

**; P<0.0001 compared with control group

\* : P<0.001 compared with control group
\*\* : P<0.0001 compared with control group

FIG. 5B

\* : P<0.001 compared with control group
\*\* : P<0.0001 compared with control group

METHOD FOR LOWERING BLOOD ALCOHOL CONCENTRATION BY ADMINISTERING AN EXTRACT OF RHUS VERNICIFLUA

CROSS REFERENCE TO RELATED APPLICATION

This application is a continuation-in-part application of U.S. Ser. No. 09/063,853 filed on Apr. 21, 1998 now U.S. Pat. No. 6,099,845.

FIELD OF THE INVENTION

The present invention relates to a method for lowering blood alcohol concentration by administering an extract of *Rhus verniciflua* to human, thereby resolving hangover, and preventing or treating alcoholic gastritis and alcohol-induced liver damage.

BACKGROUND OF THE INVENTION

Pharmaceutically useful compounds may be obtained from *Rhus verniciflua* which has been traditionally used in Korea, Japan and China in making a lacquer paint. For example, fisetin, fustin and other compounds have been found in the aqueous extract of the xylem of *Rhus verniciflua* (Hasegawa, M. and T. Shirato, *J. Chem. Soc.*, 72, 223 (1951)). Fisetin and fustin have pharmacological activity in: protecting blood vessel and capillary (Beretz, A. and Cazenave, J. P., "The Effect of Flavonoids on Blood Vessel Wall Interactions" in *Plant Flavonoids in Biology and Medicine: Biochemical, Pharmacological and Structure-Activity Relationships*, E. Middleton Jr. and J. B. Harborne, Eds., A. R. Liss, New York, pp 187–200 (1988)); suppressing the formation of peroxidized lipids (Kappus, H. et al., *Pharmacol.*, 300, 179–187 (1977); Baumann, J. et al., *Prostaglandins*, 20, 627–639 (1980); and Yoshimoto, T. et al., *Biochem. Biophys. Res. Commun.*, 116, 612–618 (1983)); and inhibiting allergy and dermatopathies (Loggia, R. D. et al., in Cody, V. et al.(eds), *Plant Flavonoids in Biology and Medicine*, A. R. Liss, New York, 481–484 (1986)).

Besides fisetin and fustin, various other flavonoids such as agathisflavone, butein, corilagin, 3',4'-dihydroxy flavone, eicosanedioic acid, europetin, sulfuretin and quercetin have also been found in the plants of genus Rhus(Bukkingham, *J. Dictionary of Natural Products*, 7, 761 (1994)). However, none of these compounds has been tested for their alcohol-decomposing activity.

Ethanol, the intoxicating component of various liquors, gives rise to various undesirable physiological and mental influences in the body, and therefore, there have been carried out a number of studies regarding its metabolic and toxicological characteristics. When imbibed, ethanol is absorbed through the gastrointestinal tract and its concentration in the blood reaches the highest level at 20 to 120 minutes after ingestion. The imbibed ethanol is then metabolized at various organs including the liver, while a small amount thereof is excreted through exhalation, urine and perspiration.

When a small amount of ethanol is ingested, it is decomposed in the liver into an acetate form by the action of alcohol dehydrogenase (ADH) and aldehyde dehydrogenase (ALDH) in cytosol and the acetate is excreted from the liver cell (Lieber, C. S., *Hepatology*, 4, 1234–1256 (1984)). A large amount of ingested ethanol, on the other hand, causes temporary accumulation of fat as well as acetaldehyde in the liver (Weiner, F. R. et al., "*Ethanol and the Liver in the Liver Biology and Pathology*", Arias, M. et al. Ed., Raven Press, New York, 1988, p1169). Acetaldehyde is a reactive, toxic substance that interferes with the metabolic process of mitochondria and inhibits the oxidative phosphorylation reaction. It also binds with membrane proteins and collagen to generate antigens (Koskinas, J. et al., *Gastroenterology*, 103, 1860 (1992)); exhibits cytotoxicity (Zetterman, R. K., "*Autoimmune Manifestation of Alcoholic Liver Diseases*", ed. Kravitt, K. I. and Wiesner, R. H., Raven Press, New York, p. 247, 1991; Takase, S. et al. *Hepatology*, 17, 9 (1993); Yokoyama, H. et al., *Hepatology*, 17, 14 (1993)); suppresses the release of proteins from the liver cell (Xu, D. S. et al., *Alcohol Alcohol*, 24, 281 (1989)); stimulates collagen biosynthesis (Pawlica, E., et al., *Arch. Toxicol.*, 65, 678 (1991)); promotes alcoholic fibrogenesis (Friedman, S. L. et al., *Hepatology*, 12, 609 (1990); and causes liver damage through the formation of macromolecular adducts (Barry, R. E., *G. I. Futures Clin. Practice*, 4, 4 (1989); Lieber, C. S., *Biochem. Soc. Trans.*, 16, 241 (1988)).

Fatty liver, promoted by excessive ethanol intake, usually results from the inhibition of the oxidative metabolism of fatty acids (Lieber, C. S., *Acta Med. Scan. Suppl.*, 703, 11 (1985); Kim, M-H. and Kwon, O-H., *Korean Biochem. J.*, 25, 499 (1992)). The increase in the blood lipid level found in animals fed with ethanol is believed to be due to the increase in VLDL (very low density lipoprotein) in the liver (Baraona, E. and Lieber, C. S., *J. Clin. Invest.*, 49, 769 (1970)) and it has also been confirmed that an oral or intravenous administration of ethanol to a human subject induces an acute increase in the level of the VLDL-containing plasma lipids (Jones, D. P. et al., *J. Lab. Clin. Med.*, 62, 675 (1963)). A high plasma lipid level was also observed in chronic alcohol abuse patients, the degree being dependent on the duration and the amount of ethanol ingested (Schapiro, R. H., et al., *J. Clin. Invest.*, 43, 1338 (1964)). The accumulation of fat in the liver interferes with the liver's metabolic function and leads to fibrogenesis and damaged liver cells.

Carbon tetrachloride ($CCl_4$) induces liver damage and is used in various animal and cultured cell tests to evaluate agents for treating hepatic disorders. $CCl_4$ converts to a radical species, $CCl_3$, by the action of such a metabolic enzyme as cytochrome P450 and the radical induces oxidation of the fat in the liver or the fatty acids present in the phospholipid membrane. This oxidative process is participated by oxygen to form lipid peroxides. This peroxidation process, in turn, brings about fat accumulation, lowering of protein secretion, degradation of glycogen, destruction of enzymes, and eventually, the death of liver cells. Accordingly, $CCl_4$-induced liver damage is used as a model in tests to evaluated liver disorders caused by ethanol (Recknagel, R. O., *Pharmacol. Rev.*, 19, 145–208 (1967); Alpers et al., *Mol. Pharmacol.*, 4, 566–573 (1968); Slater, *Free Radicals, Lipid Peroxidation and Cancer*, Academic Press, London, p 243 (1982); Chang, I. M. et al., *Drug and Chemical Toxicology*, 6(5), 443–453 (1989)).

Stomach lesion, ulcer, or cancer usually progresses from gastric mucosal injuries caused by such factors as psychological stress, excessive intake of ethanol, *Helicobacter pyloris* (Suzuki, M. and S. Miura, *Nippon Rinsho*, 15(12), 3154–3158 (1993)), and thyrotropin-releasing hormone (TRH). Nicotine also damages the gastric mucous membrane and smokers are known to have a 55% higher risk of getting stomach cancer than non-smokers (Kneller, R. W. et al., *J. Natl. Cancer Inst.*, 84(16), 1261–1266 (1992)).

It has been reported that the administration of adenosine to rats having ethanol-induced gastric mucous membrane damage at a dosage of 7.5 mg/kg is effective in restoring the damaged membrane through increased blood circulation therethrough (Cho, C. H., *Acta Physiol. Hung*, 80(1–4): 175–180 (1992)). Also, polysaccharides extracted from ginseng leaves and roots have been described to exhibit dosage-dependent therapeutic effects in treating HCl- or ethanol-induced gastric mucous membrane injuries (Sun, X. B. et al., *Planta Med.*, 58(5), 445–448 (1992)). There have been conducted many animal tests to evaluate cures for gastric lesions of two types; stress-induced and ethanol-induced. Although these two types are of similar nature, there exists a significant difference in terms of therapeutic method. For example, prostaglandin is more effective in treating the ethanol-induced gastric injury, while in the stress-induced case, cimetidine is.

The present inventors have unexpectedly found that an acetone extract of *Rhus verniciflua* is a potent agent for lowering the blood alcohol level and it is capable of treating or preventing alcohol-induced damage of the liver or stomach.

SUMMARY OF THE INVENTION

Accordingly, it is an object of the present invention to provide a method for lowering blood alcohol concentration by administering an extract of *Rhus verniciflua* to human.

Another object of the present invention is to provide a method for resolving hangover by administering an extract of *Rhus verniciflua* to human.

An additional object of the present invention is to provide a method for preventing alcoholic gastritis by administering an extract of *Rhus verniciflua* to human.

A further object of the present invention is to provide a method for protecting the liver from alcohol-induced damage by administering an extract of *Rhus verniciflua* to human.

BRIEF DESCRIPTION OF THE DRAWINGS

The above and other objects and features of the present invention will become apparent from the following description of the invention, when taken in conjunction with the accompanying drawings, in which:

FIGS. 5A and 5B present the activity of an acetone extract of *Rhus verniciflua* in preventing $CCl_4$-induced liver damage, wherein FIG. 5A shows its effect on the serum AST concentration and FIG. 5B, its effect on the serum ALT concentration; and FIGS. 6A and 6B illustrate the activity of an acetone extract of *Rhus verniciflua* in preventing ethanol-induced gastric lesion, wherein FIG. 6A shows the stomach of a normal rat (control) and FIG. 6B, the stomach of a rat treated with the acetone extract of *Rhus verniciflua*.

DETAILED DESCRIPTION OF THE INVENTION

In accordance with the present invention, there is provided a method for lowering blood alcohol concentration by administering an extract of *Rhus verniciflua* to human.

The acetone extract of *Rhus verniciflua* of the present invention is prepared as follows. The woody part of *Rhus verniciflua* is cut and dried in the shade for 1 week to 3 months, preferably, 1 month. The dried woody part may be crushed, if necessary. Otherwise, the woody part of the *Rhus verniciflua* may be processed into the form of wood chips or sawdust without the drying process.

To 100 g of the processed woody part of the *Rhus verniciflua*, an organic solvent is added in an amount ranging from 0.3 to 1 l, and the mixture is allowed to stand at a temperature ranging from 20 to 60° C., preferably, 40° C., for a period ranging from 1 to 30 days, preferably, 5 days, to obtain a yellow crude extract. Exemplary organic solvent useful in the present invention includes acetone, ethanol, methanol and a mixture thereof, wherein acetone is preferred. Acetone is preferably an acetone-based solvent having an acetone content of 80% or more, preferably 90% or more, and ethanol is preferably an ethanol-based solvent having an ethanol content of 80% or more, preferably, 90%.

Then, water is added to the crude extract, and the mixture is partitioned to obtain a water-soluble fraction. The water-soluble fraction is filtered and then concentrated.

The resulting concentrate is dried, dissolved in an organic solvent, e.g., methanol, and subjected to silica gel adsorption column chromatography using as an eluent a mixture of chloroform and methanol, preferably mixed in a ratio ranging from 9:1 to 7:3 (v/v), until the yellow extract is completely eluted. The combined extract is concentrated under a reduced pressure and then dried to obtain the inventive *Rhus verniciflua* extract.

Figure 1:
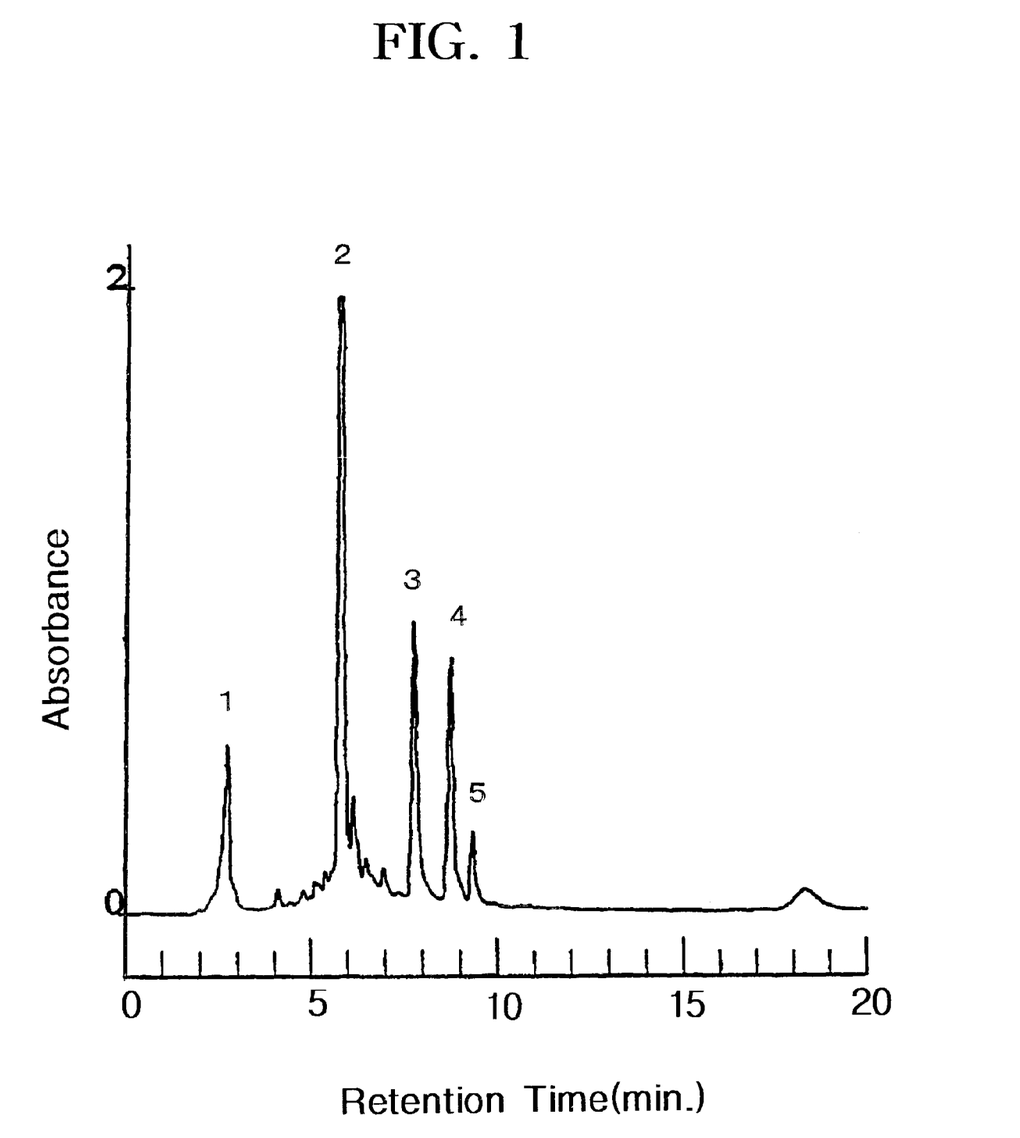
FIG. 1 shows a high pressure liquid chromatography (HPLC) scan of the extract of *Rhus verniciflua*.

Analysis by high pressure liquid chromatography(HPLC) revealed that the inventive extract is a mixture consisting of five components. FIG. 1 shows an HPLC scan of the extract of *Rhus verniciflua*, wherein Peak 1 is a novel compound having a molecular weight of 162; Peak 2, fustin(3,3',4',7-tetrahydroxyflavanone) having a molecular formula of $C_{15}H_{12}O_6$(Mw: 288); Peak 3, fisetin(3,3',4',7-tetrahydroxyflavone) having a molecular formula of $C_{15}H_{10}O_6$(Mw: 286); Peak 4, sulfuretin (3',4',6'-trihydroxyaurone) having a molecular formula of $C_{15}H_{10}O_5$ (Mw: 272); and Peak 5, butein(2',3,4,4'-tetrahydroxychalcone) having a molecular formula of $C_{15}H_{12}O_5$ (Mw: 272).

The inventive extract of *Rhus verniciflua* obtained as above exhibits an alcohol-decomposing activity, thereby lowering blood alcohol concentration in human. Accordingly, the inventive extract may be employed as a pharmaceutical agent for resolving hangover, preventing alcoholic gastritis and protecting liver from an alcoholic damage.

Accordingly, the present invention also provides a pharmaceutical composition for use as a blood alcohol concentration-lowering agent, hangover resolving agent, alcoholic gastritis preventive agent and liver protective agent, which comprises the extract of *Rhus verniciflua* as an active ingredient, in combination with pharmaceutically acceptable excipients, carriers or diluents.

A pharmaceutical formulation may be prepared by using the composition in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical formulation of the present invention can be administered via various routes including oral, transdermal, subcutaneous, intravenous and intramuscular introduction. For treating a human patient, a typical daily dose of the extract of Rhus verniciflua may range from about 10 to 100 mg/kg body weight, preferably 15 to 60 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The present invention also provides a method for lowering blood alcohol concentration by administering the inventive extract of Rhus verniciflua to human, thereby resolving hangover, and preventing or treating alcoholic gastritis and alcohol-induced liver damage.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Preparation of Extract of Rhus verniciflua
(Step 1) Preparation of Crude Extract Rhus verniciflua was cut into 10 cm-long pieces and dried in the shade for 1 month. 4 l of 99.9% acetone was added to 400 g of the dried Rhus verniciflua and the mixture was allowed to stand at 40° C. for 5 days to obtain a yellow extract. To the extract was added an equal volume of water and the mixture was stirred at 40° C. and then cooled to room temperature. The resulting mixture was filtered through No. 2 filter(Watman, U.S.A.) and the filtrate was concentrated at a reduced pressure using a rotary vacuum evaporator(Labo rota 300, Resona Co., Swiss). The concentrate was dried with a centrifugal vacuum drier(Centrabag vision, Korea) to obtain 4.4 g of a crude extract(yield: 1.1%).
(Step 2) Silica Gel Adsorption Chromatography
The crude extract obtained in Step 1 was purified by silica gel adsorption chromatography as follows. 40 g of silica gel (230–400 mesh, for chromatographic use, Merck) which had previously been activated at 130° C. for 3 hours was slurried in n-hexane, and then packed in a glass column (2.9×45 cm). For the purpose of removing moisture in the crude extract, 7 g of calcium sulfate was filled in the top portion of the column. 4 g of the crude extract was dissolved in 6 ml of methanol, loaded on the column, and then using a chloroform:methanol mixture(90:10 (v/v)) the yellow extract was eluted completely. Yellow eluates were combined and concentrated under a reduced pressure with a rotary vacuum evaporator(Labo rota 300, Resona Co., Swiss), and dried at 40° C. with a centrifugal vacuum drier(Centrabag vision, Korea) to obtain 3 g of a crude extract(yield: 75%).

EXAMPLE 2

Analysis of Extract of Rhus verniciflua
(Step 1) Resolution of Components by High Pressure Liquid Chromatography The extract of Rhus verniciflua obtained in Example 1 was mixed with an equal volume of methanol. The mixture was pre-treated with $C_{18}$-type Sep-pak(Waters, U.S.A.) and then filtered through a 0.2 μm syringe filter(Satorius, Germany). The filtrate was injected to DX-300 Bio HPLC (Dionex) equipped with an RCM 8×10 column(Waters, U.S.A.) and a $C_{18}$ 8×10 cartridge column (Nova-Pak) and then eluted using a mixture of water and methanol under the condition listed in Table 1. The chromatography was conducted with a sample size of 50 μl, and the eluate was detected at 254 nm with a DX-300 UV detector.

TABLE 1

| Time (min) | Flow rate (ml/min) | Eluent Water (%) | Methanol (%) | Curve |
|---|---|---|---|---|
| 0.0 | 1.5 | 80 | 20 | 5 |
| 0.5 | 1.5 | 80 | 20 | 5 |
| 3.0 | 1.5 | 50 | 50 | 5 |
| 12.8 | 1.5 | 20 | 80 | 5 |
| 14.9 | 1.5 | 0 | 100 | 5 |
| 16.7 | 1.5 | 0 | 100 | 5 |
| 18.6 | 1.5 | 80 | 20 | 5 |
| 20.0 | 1.5 | 80 | 20 | 5 |

The resulting HPLC chromatogram shown in FIG. 1 reveals that the extract of Rhus verniciflua is a mixture of five components shown in Table 2.

TABLE 2

| Component | Peak 1 | Peak 2 | Peak 3 | Peak 4 | Peak 5 |
|---|---|---|---|---|---|
| Content (%) | 10.00 | 40.69 | 10.80 | 9.56 | 2.43 |

(Step 2) Analysis of Respective Components

Each component obtained in Step 1 was analyzed by the combined use of a mass spectrometer (JEOL JMS-AX 505 WA, Japan; Injection: direct injection, Ion mode: EI+, Temp.: 71.4° C., Output m/z range: 50–302) and an elemental analyzer(Perkin-Elmer, U.S.A.). The results exhibited that Peak 1 is a novel compound having a molecular weight of 162; Peak 2, fustin (3,3',4',7-tetrahydroxyflavanone) having a molecular formula of $C_{15}H_{12}O_6$ (Mw: 288)(white crystals); Peak 3, fisetin(3,3',4',7-tetrahydroxyflavone) having a molecular formula of $C_{15}H_{10}O_6$(Mw: 286)(yellow crystals); Peak 4, sulfuretin(3',4',6'-trihydroxyaurone) having a molecular formula of $C_{15}H_{10}O_5$ (Mw: 272) (deep orange crystals); and Peak 5, butein(2',3,4,4'-tetrahydroxychalcone) having a molecular formula of $C_{15}H_{12}O_5$(Mw: 272)(orange crystals).

EXAMPLE 3

Activity of the Extract of R. verniciflua in Lowering Blood Alcohol Concentration Ten three-week old Sprague-Dawley rats were put on a 24-hour fast while allowing their access to water. Thereafter, 10 ml/kg of 40% ethanol was orally administered to each rat by force with a 10 cm stainless steel sonde and the rats were divided into two groups, each containing five. After 1 hour, the rats of one group were orally administered with 2 ml of water(Control group) and those of the other group, with 2 ml of 500 mg/ml aqueous solution of the extract of *Rhus verniciflua* prepared in Example 1 (Test group). After 4 hour, blood samples were taken from the hearts of the rats and the blood alcohol concentration was measured by employing a kit for determining blood alcohol concentration (Sigma 332, U.S.A., Ultraviolet, Endpoint method).

Figure 2:
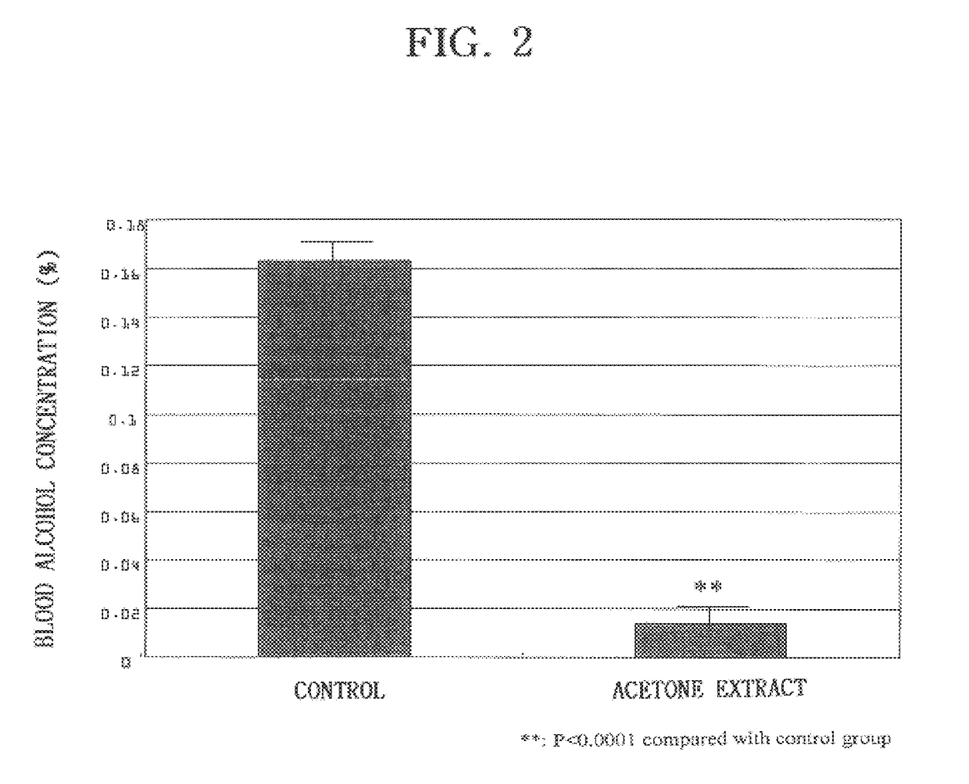
FIG. 2 depicts the ethanol decomposing activity of an acetone extract of *Rhus verniciflua* in comparison with that of a control.

FIG. 2 displays the activity of the extract of *Rhus verniciflua* in lowering the blood alcohol concentration in comparison to that of the non-treated Control group. While the blood alcohol concentration of the Control group is 0.162%, that of the Test group is only 0.014%. Accordingly, it has been confirmed that the extract of *Rhus verniciflua* lowers the blood alcohol concentration by a factor of more than 10 as compared with the control.

Figure 3:
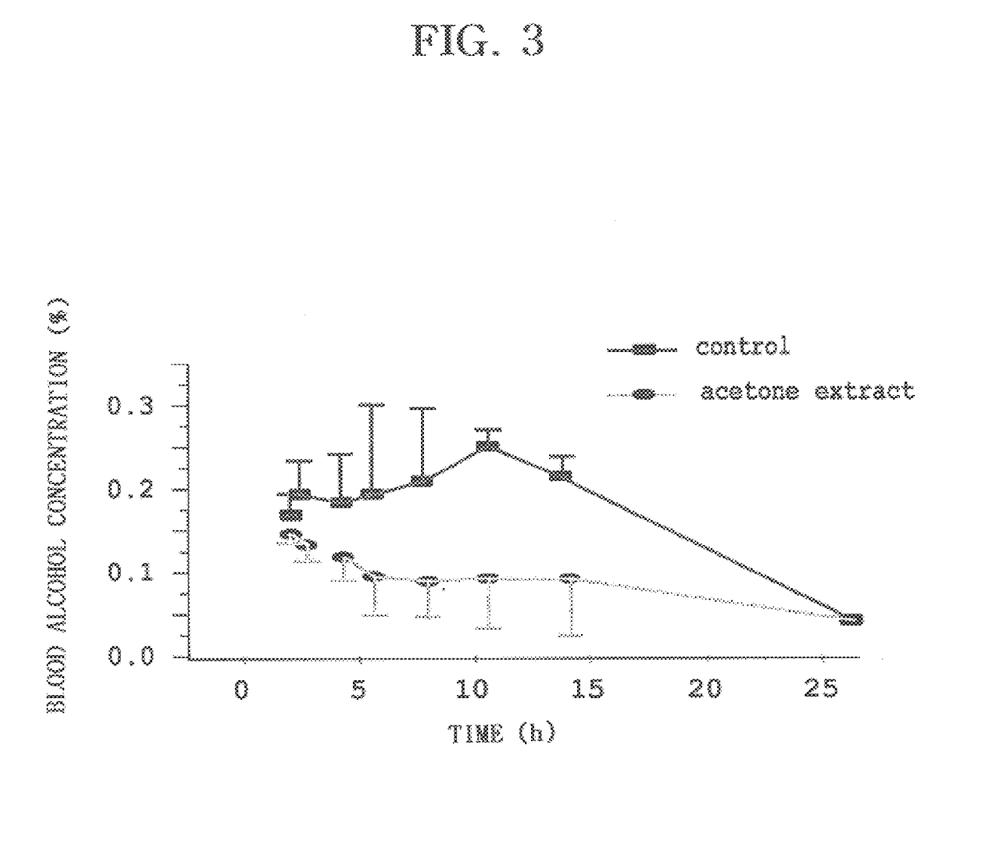
FIG. 3 represents the time-dependent activity of an acetone extract of *Rhus verniciflua* in lowering blood ethanol concentration in rats.

Further, periodic blood samples were taken from the rats of the two groups at pre-determined time intervals after the administration of ethanol to determine the variation in the blood alcohol concentration with time. As shown in FIG. 3, the blood alcohol concentration in the rats of the Control group reaches the highest level at 10 hours after the alcohol administration, while the rats of the Test group showed remarkably lower blood ethanol concentration after 5 hours.

EXAMPLE 4

Activity of the Extract of *R. verniciflua* Increasing Alcohol Dehydrogenase Activity The Activity of alcohol dehydrogenase was determined based on the change in the absorbance which depends on the amount of NAD reduced under the presence of an excessive amount of alcohol.

Rats were administered with 40% ethanol, and then with water(Control group) or the extract of *R. verniciflua* (Test group) as in Example 3, followed by suffocating them to death in $CO_2$ at 4 hours after the administration. The liver was extracted from each rat, washed with physical saline and then weighed. The liver was put in a 10-fold volume of 0.1 M potassium phosphate buffer (pH 7.4) containing 0.154 M KCl and homogenized by a Teflon-glass homogenizer. The homogenate was centrifuged at 40° C., 9,000×g for 30 min. to obtain a supernatant. The supernatant was subjected to an ultracentrifuge at 4° C., 110,000×g for 1 hour to obtain a supernatant as a cytosol fraction.

2 mg of cytosol fraction was added to a reaction mixture containing 55 mM sodium phosphate buffer (pH 7.4), 20 mM ethanol, 0.2 mM NAD and the resulting mixture was reacted at 37° C. for 5 min. The absorbance was measured at 340 nm for 3 min. and plotted against time, and the activity of alcohol dehydrogenase was determined from the slope of the curve in accordance with the method of Crow et al. (Crow, K. E. and M. J. Hardman, "Regulation of Rates of Ethanol Metabolism in Human" in *Human Metabolism of Alcohol*, Crow, K. E. and Batt, R. D.(eds), Vol. II, FL. CRC Press, p3(1989)).

Figure 4:
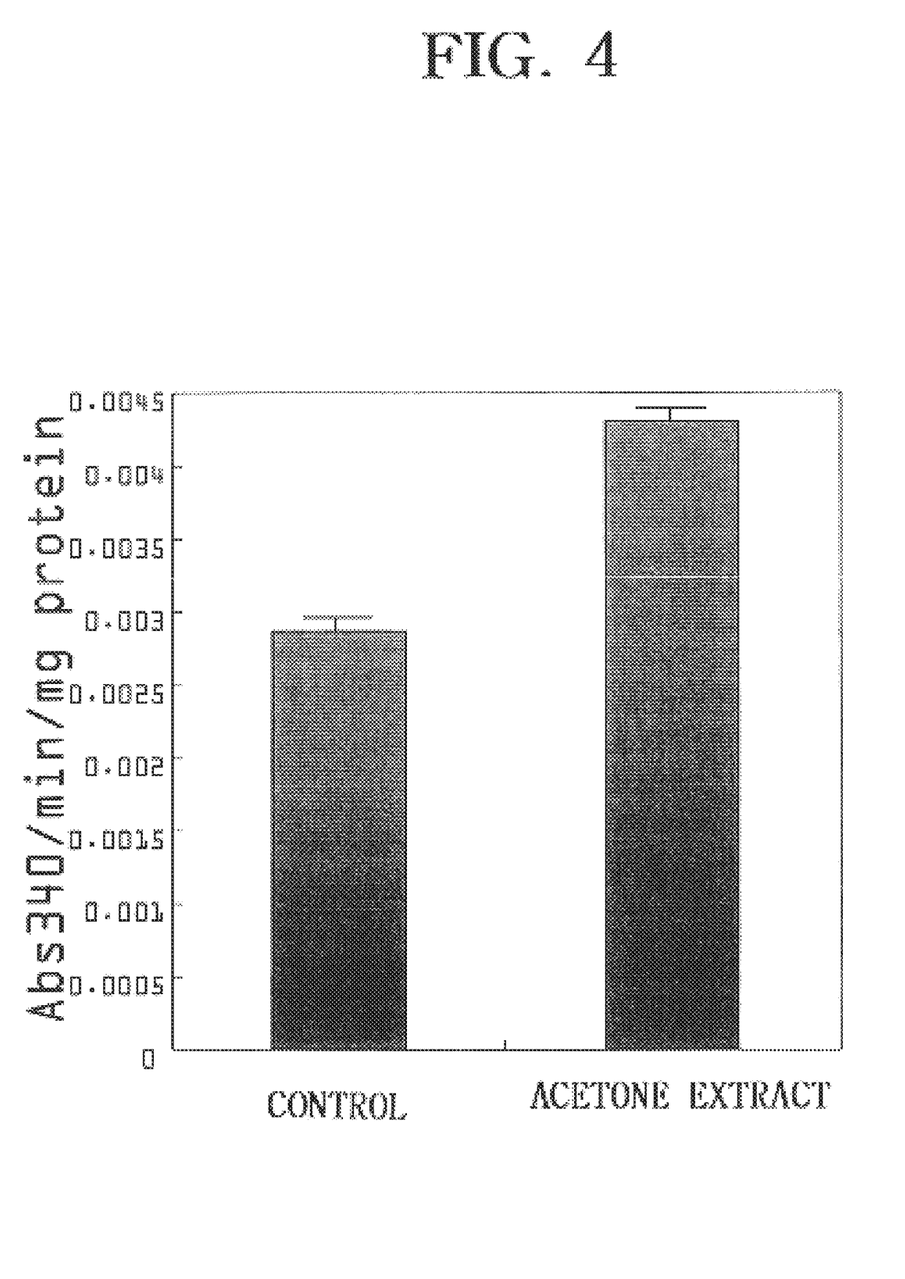
FIG. 4 discloses the alcohol dehydrogenase activity in the rat treated with an acetone extract of *Rhus verniciflua* in comparison with that of a control.

The result in FIG. 4 shows that the activity of alcohol dehydrogenase increases in the rats administered with the extract of *R. verniciflua* in comparison with the Control group.

EXAMPLE 5

Liver Protective Activity of the Extract of *R. verniciflua*

$CCl_4$ has a hepatotoxicity and is used as a test material for screening materials having liver protective activity. The extract of *R. verniciflua* was tested for its activity in protecting liver from the toxic effect of $CCl_4$, as follows.

Male Sprague-Dawley rats were bred under a condition of 23±2° C., relative humidity of 55±10%, and light period of 12 hours, while allowed free access to animal fodder (Purina Korea) and water.

The rats were divided into three groups and rats of one group were peritoneally injected with 0.3 ml/kg of a mixture of polyethylene glycol:saline (1:2(v/v)) once a day for 4 days (Control group). The rats of a second group were peritoneally injected once with 0.3 ml/kg of $CCl_4$ (Comparative group), and those of the remaining group, once with 0.3 ml/kg of $CCl_4$ and then once a day for 4 days with 20 mg/kg of the extract of *R. verniciflua* prepared in Example 1 (Test group).

Thereafter, the degree of hepatotoxicity was determined by measuring the concentrations of serum aspartate transaminase (AST) and alanine transaminase (ALT), which increase upon the occurrence of hepatotoxicity, by employing Refletron S system (Boeringer Mannheim Co., Ltd., Osaka, Japan).

Figure 5A:
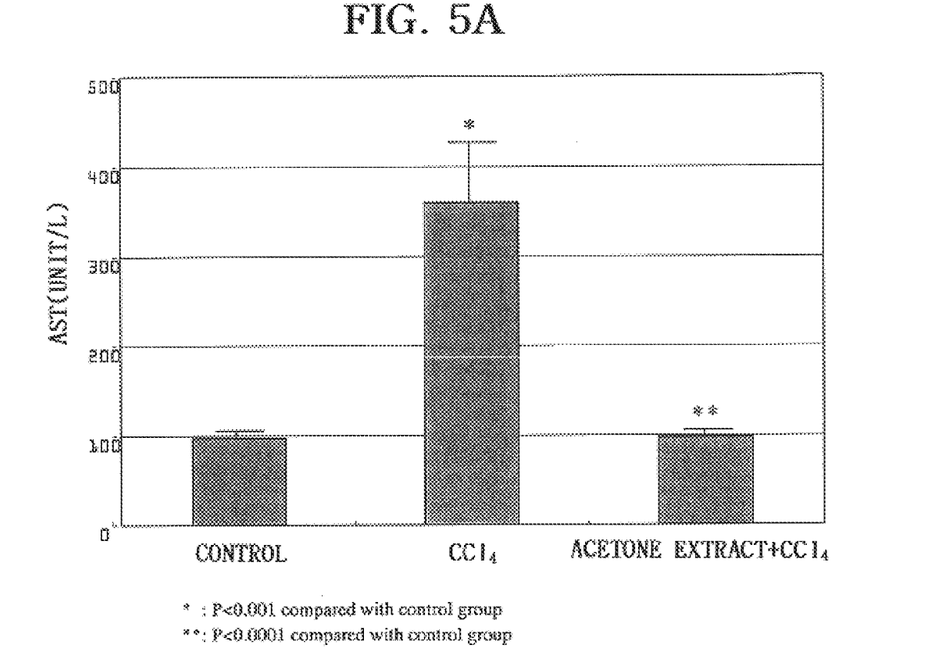
Figure 5B:
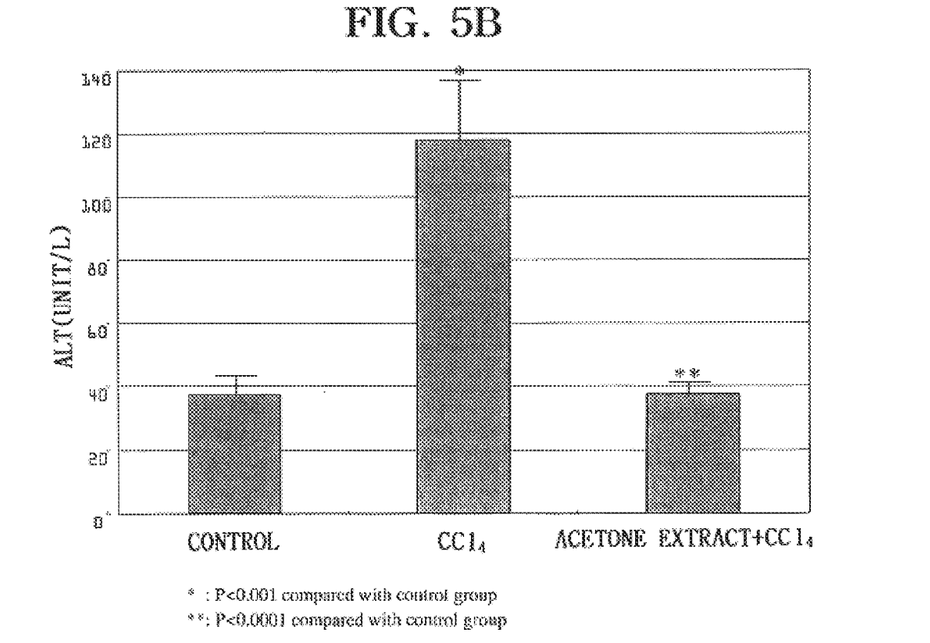

The results in FIGS. 5A and 5B exhibit that the AST and ALT levels in the rats of the Test group are similar to those of the Control group, while those of the Comparative group are much higher than the other two groups. These results demonstrate that the acetone extract of *R. verniciflua* protects the liver from the damage caused by ingestion of an alcohol.

EXAMPLE 6

Activity of the Extract of *R. verniciflua* Preventing Alcoholic Gastritis

Twenty 8-week old male specific pathogen free(SPF) Sprague-Dawley rats (Korea Test Animals Co., Ltd.) each weighing about 200 g were put on a 24-hour fast. The rats were divided into four groups, each containing five.

Consequently, the extract of *R. verniciflua* prepared in Example 1 was suspended in 10% hydroxypropyl-methylcellulose (HPMC) and administered orally to rats of three groups in amounts corresponding to 100, 300 and 1,000 mg/kg of the extract, respectively (Test groups 1, 2 and 3, respectively). The rats of the remaining group were administered orally with 2 ml of 10% HPMC (Control group). After one hour, the rats were orally administered with 1.5 ml of absolute ethanol to injure the gastric tissue.

One hour after the administration of ethanol, the rats were anesthetized to death with ether. The stomach was taken therefrom, injected with 14 ml of 1% formalin and fixed in 1% formalin for one hour. The stomach was incised along with the largest swelled region and spread, and the area ($mm^2$) of gastric lesion was measured by a caliper. Inhibition (%) of lesion was calculated by the following equation and $ED_{50}$(mg/kg) was deduced therefrom by employing a linear regression method:

$$\text{Inhibition (\%)} = \left[ \frac{\text{Gastric lesion of the Control group} - \text{Gastric lesion of the Test group}}{\text{Gastric lesion of the Control group}} \right] \times 100$$

The result in Table 3 shows that the extract of *Rhus verniciflua* has a preventive activity on alcoholic gastritis. Specifically, the rats of Test groups 1, 2 and 3 exhibited gastric lesion inhibition (%) of 43.5%, 68.5% and 78.8%, respectively.

TABLE 3

| Group | Dose of extract (mg/kg) | Gastric lesion (mm$^2$) | Inhibition (%) | ED$_{50}$ (mg/kg) |
|---|---|---|---|---|
| Control group | — | 84.2 ± 2.2 | — | — |
| Test group 1 | 100 | 47.6 ± 10.1 | 43.5 | 121 |
| Test group 2 | 300 | 28.3 ± 8.3 | 68.5 | |
| Test group 3 | 1,000 | 15.8 ± 3.8 | 78.8 | |

Figure 6A:
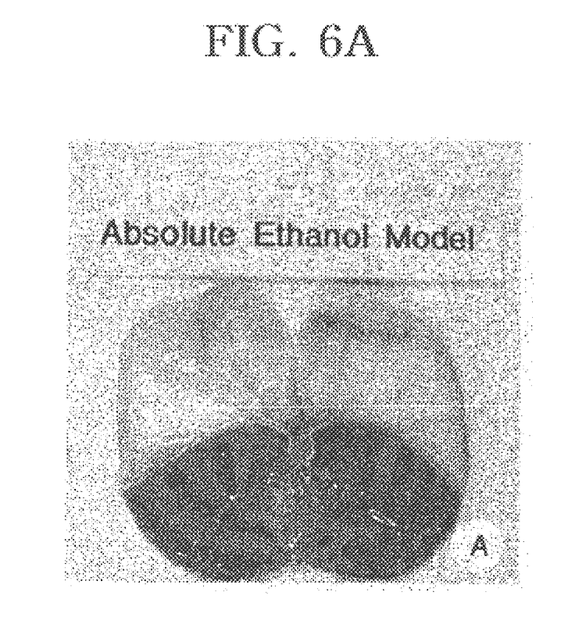
Figure 6B:
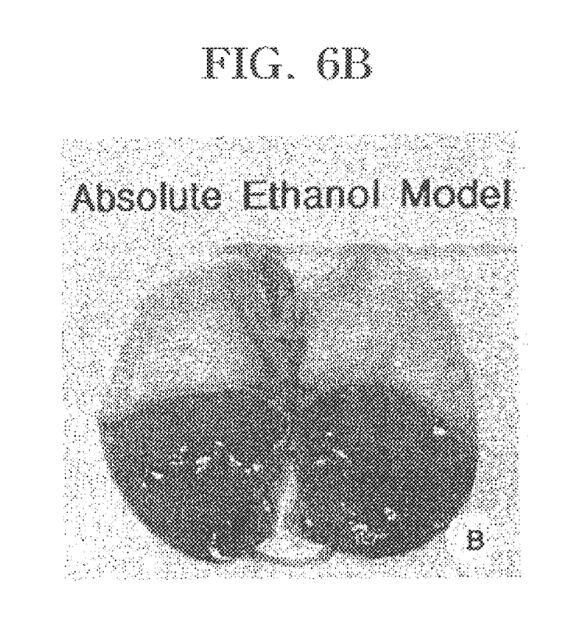

Further, the spread stomachs of the rats of Control group and Test group 3 were photographed. The result in FIGS. 6A and 6B shows that the stomach of the rat of Control group has streaky lesions, while that of Test group 3 does not. This result also demonstrates that the extract of *Rhus verniciflua* protects gastric tissues from ethanol-induced injury.

EXAMPLE 7

Acute Toxicity of the Extract of *Rhus verniciflua*

4-week old specific pathogen free (SPF) Sprague-Dawley rats were acclimated for 1 week in an environmental safety cabinet (FLUFLANGCE) and healthy rats were selected for the test. The rats were grouped by 5 rats and put into a polycarbonate breeding case (26×42×18 cm) which was maintained at 23±3° C., relative humidity of 50±10%, ventilation of 10–20 times/hour, light period of 12 hour, and luminous intensity of 300–500 Lux. The rats were allowed free access to sterilized laboratory animal food (Shinchon Feed, Korea) and water.

Before the test, the rats were put on a 18-hour fast. Five groups of rats were then orally administered once with 20 ml/kg of suspensions containing 5.0, 3.3, 2.2, 1.5 and 1.0 g/kg of the extract of *Rhus verniciflua* in 0.5% sodium carboxymethyl cellulose. Thereafter, the lethality of the rats were observed for 14 days.

The result in Table 4 shows that the extract of *Rhus verniciflua* does not show acute toxicity at a dose of 5 g/kg and below.

TABLE 4

| Dose (g/kg) | No. of dead rats/No. of tested rats |
|---|---|
| 1.0 | 0/5 |
| 1.5 | 0/5 |
| 2.2 | 0/5 |
| 3.3 | 0/5 |
| 5.0 | 0/5 |

While the invention has been described with respect to the above specific embodiments, it should be recognized that various modifications and changes may be made to the invention by those skilled in the art which also fall within the scope of the invention as defined by the appended claims.

What is claimed is:

1. A method for lowering blood alcohol concentration in human to prevent or treat a disease or disorder caused by intake of ethanol, comprising administering an extract of *Rhus verniciflua* thereto, said extract containing fustin, fisetin, sulfuretin and butein and being prepared by a process which includes the steps of: (a) adding an acetone-based solvent to the woody part of *Rhus verniciflua*, (b)-allowing the mixture to stand at 20 to 60 for 1 to 30 days to obtain a crude extract, (c) adding water to the crude extract and filtering the resulting mixture to obtain a filtrate, and (d) subjecting the filtrate to silica gel adsorption chromatography employing as an eluent a mixture of chloroform and methanol having a mixing ratio ranging from 9:1 to 7:3 (v/v) to obtain the extract of *Rhus verniciflua*.

2. The method of claim 1, wherein the disease or disorder is selected from the group consisting of hangover, alcoholic gastritis and alcohol-induced liver damage.

3. The method of claim 1, wherein the acetone based solvent in step (a) has an acetone-content of 80% or more.

* * * * *